(12) United States Patent
DeBusk et al.

(10) Patent No.: US 10,990,772 B2
(45) Date of Patent: Apr. 27, 2021

(54) MAINTAINING MEDICAL DEVICE CHAIN OF CUSTODY USING MULTIPLE IDENTIFICATION ENCODING TECHNOLOGIES

(71) Applicant: DeRoyal Industries, Inc., Powell, TN (US)

(72) Inventors: Brian C. DeBusk, Knoxville, TN (US); Joe L. Smith, Powell, TN (US); Mary E. Kaylor, Chattanooga, TN (US)

(73) Assignee: DeRoyal Industries, Inc., Powell, TN (US)

( * ) Notice: Subject to any disclaimer, the term of this patent is extended or adjusted under 35 U.S.C. 154(b) by 1285 days.

(21) Appl. No.: 15/041,484

(22) Filed: Feb. 11, 2016

(65) Prior Publication Data

US 2017/0235896 A1 Aug. 17, 2017

(51) Int. Cl.
| | |
|---|---|
| *G06K 7/10* | (2006.01) |
| *G16H 40/20* | (2018.01) |
| *G06Q 10/08* | (2012.01) |
| *G16H 40/67* | (2018.01) |
| *G16H 10/60* | (2018.01) |
| *G16H 50/20* | (2018.01) |
| *G06K 7/14* | (2006.01) |

(Continued)

(52) U.S. Cl.
CPC ......... *G06K 7/10366* (2013.01); *G06Q 10/08* (2013.01); *G06Q 10/083* (2013.01); *G06Q 10/087* (2013.01); *G06Q 10/0875* (2013.01); *G16H 40/20* (2018.01); *G06F 16/9554* (2019.01); *G06K 7/1413* (2013.01); *G06K 7/1417* (2013.01); *G06K 19/06037* (2013.01); *G06Q 20/203* (2013.01); *G16H 10/60* (2018.01); *G16H 40/67* (2018.01); *G16H 50/20* (2018.01)

(58) Field of Classification Search
CPC .. G06K 7/10366; G16H 40/20; G06Q 20/203; G06Q 10/087; G06Q 10/08; G06Q 10/083; G06Q 10/0875
USPC .......................................................... 705/28
See application file for complete search history.

(56) References Cited

U.S. PATENT DOCUMENTS

| | | | |
|---|---|---|---|
| 2004/0046020 A1* | 3/2004 | Andreasson | A61J 1/14 235/385 |
| 2008/0030345 A1* | 2/2008 | Austin | A61B 90/90 340/572.8 |
| 2014/0048593 A1 | 2/2014 | Hoganson | |

OTHER PUBLICATIONS

Gamaleldin, Ahmed. RFID in retail stores and B2B supply chains—a survey and an advisory expert system development for investors. Long Island University, The Brooklyn Center, ProQuest Dissertations Publishing, 2009. 1463317.*

* cited by examiner

*Primary Examiner* — Nathan C Uber
*Assistant Examiner* — Fawaad Haider
(74) *Attorney, Agent, or Firm* — Luedeka Neely Group, PC

(57) ABSTRACT

An inventory management system provides automated management of medical item inventory and maintenance of a digital chain of custody for medical items. Medical items are labeled with an RFID-encoded tag that also displays a 2D barcode. The RFID tag and the 2D barcode both encode the same serialized Electronic Product Code (EPC) data for each specific item. Reading of the RFID tag is performed using a fixed or handheld RFID reader. Reading of the 2D barcode is performed using a handheld mobile device, such as a tablet or smart phone. The two-technology label allows for the digital chain of custody to be updated by means of RFID scanning in locations where RFID readers are available and (Continued)

by using a smart phone or tablet to read the 2D barcode in locations where RFID readers are unavailable.

13 Claims, 2 Drawing Sheets

(51) Int. Cl.
    *G06Q 20/20*     (2012.01)
    *G06F 16/955*    (2019.01)
    *G06K 19/06*     (2006.01)

MAINTAINING MEDICAL DEVICE CHAIN OF CUSTODY USING MULTIPLE IDENTIFICATION ENCODING TECHNOLOGIES

FIELD

This invention relates to the field of medical item inventory management. More particularly, this invention relates to a system for maintaining a chain of custody of medical devices.

BACKGROUND

Hundreds of millions of dollars in expensive medical devices exchange hands each year. Such devices are shipped to sales representatives, distributors, hospital materials management, and clinicians. Delivery of a medical device to a particular person in a particular location does not always mean that the device will remain in the custody of the receiving person. The device often changes hands between multiple persons and at multiple locations. This commonly occurs when medical device sales representatives share inventory.

Because of the high cost and often limited availability of stock, medical device inventory is frequently shared within a defined area by multiple sales representatives. Typically, this inventory is managed manually and may be stored in a tote bag or box in locations under control of the sales representative, such as in the representative's home or car.

Inventory may also be managed in an automated fashion, such as using RFID identification technology. This is a proven and preferred option for locations such as hospitals. Items may be stored in access-controlled areas where RFID tags are read by fixed or handheld RFID readers. Problems can arise when deploying this type of technology in the field for inventory management. Some of the issues with deploying handheld RFID readers to sales representatives in the field include the high cost of the readers, complications associated with hardware maintenance, and the ability to manage items without stray RFID reads.

What is needed, therefore, is a system for maintaining an inventory of medical devices using multiple identification encoding technologies appropriate for hospital and field applications, including lower cost and less complicated identification technology for users in the field.

SUMMARY

Embodiments of the present invention provide automated management of medical item inventory and maintenance of a digital chain of custody for medical items. In a preferred embodiment, items are labeled with an RFID-encoded tag that also displays a 2D barcode. The chip contained within the RFID tag and the 2D barcode both encode the same serialized Electronic Product Code (EPC) data for each specific item. Reading of the RFID tag is performed using a fixed or handheld RFID reader. Reading of the 2D barcode is performed using a handheld mobile device, such as a tablet or smart phone. The two-technology label allows for the digital chain of custody to be updated by means of RFID scanning in locations where RFID readers are available and by using a smart phone or tablet to read the 2D barcode in locations where RFID readers are unavailable.

The above and other needs are met by a method for maintaining a chain of custody of medical items that each have an RFID tag and an optical code attached thereto, both of which encode a unique identifier that uniquely identifies a medical item. In one embodiment, the method includes:

(a) performing a scan of an interior space of a shielded enclosure in which the medical items are stored, the scan performed using an RFID reader;

(b) based on the scan of step (a), determining that a first medical item has been removed from the shielded enclosure;

(c) based on a determination that the first medical item has been removed from the shielded enclosure, updating the chain of custody of the first medical item by associating the unique identifier of the first medical item with first user identification information in a medical item inventory database, where the first user identification information identifies a first user who removed the first medical item from the shielded enclosure;

(d) scanning the optical code attached to the first medical item using a mobile computing device associated with a second user;

(e) decoding the unique identifier encoded in the optical code attached to the first medical item using the mobile computing device; and (f) updating the chain of custody of the first medical item by associating in the medical item inventory database the unique identifier decoded in step (e) with second user identification information that identifies the second user.

In another aspect, the invention provides an apparatus for maintaining a chain of custody of medical items that each have an RFID tag and an optical code attached thereto, both of which encode a unique identifier that uniquely identifies a medical item. In a preferred embodiment, the apparatus includes a shielded enclosure having an internal space for receiving the medical items. The shielded enclosure is configured to attenuate radio frequency signals emanated from RFID tags disposed outside the shielded enclosure to levels that are substantially undetectable within the internal space. Disposed within the internal space of the shielded enclosure are one or more RFID antennas that receive radio frequency signals emanated from RFID tags attached to the medical items disposed within the internal space. The radio frequency signals contain the unique identifiers encoded in the RFID tags. At least one RFID reader is electrically connected to the one or more RFID antennas. The RFID reader decodes the unique identifiers contained in the radio frequency signals emanated from the RFID tags.

The apparatus also includes an inventory computer having a processor for executing instructions for receiving the unique identifiers decoded by the RFID reader and determining based thereon that a first medical item has been removed from the shielded enclosure. The apparatus includes a medical item inventory database in which a chain of custody of medical items is maintained by associating unique identifiers of medical items with user identification information that identifies users having custody of medical items. The apparatus also includes an inventory management server that, based on a determination that the first medical item has been removed from the shielded enclosure, operates on the medical item inventory database to update a chain of custody of the first medical item. The chain of custody is updated by associating the unique identifier of the first medical item with first user identification information that identifies a first user who removed the first medical item from the shielded enclosure.

The apparatus also includes a mobile computing device associated with a second user. The mobile computing device is operable to scan the optical code attached to the first medical item, decode the unique identifier encoded in the optical code, and transmit a message to the inventory management server containing the unique identifier and second user identification information that identifies the second user. The inventory management server is operable to receive the unique identifier of the first medical item and the second user identification information and operate on the medical item inventory database to update the chain of custody of the first medical item by associating the unique identifier of the first medical item with the second user identification information.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

As the term is used herein, a "medical item" is an item, device, material, substance, or piece of durable medical equipment (DME) that may be used or consumed during the performance of a medical procedure or that is dispensed to a patient to treat a medical condition or provide comfort to the patient. For example, a surgical implant is a medical item. Knee braces, negative pressure wound therapy units, blood glucose monitors, and wheelchairs are further examples of medical items. Sponges, gloves and drapes are also medical items.

Each medical item has a unique identifier, such as an Electronic Product Code (EPC), encoded in an RFID tag and in a 2D barcode attached to the medical item or its packaging. In a preferred embodiment, the RFID tag and 2D barcode are combined in a single label attached to the medical item or its wrapper.

As the term is used herein, a "scan" for RFID tags refers to operations performed by an RFID reader to transmit signals and receive signals from RFID tags that are in range of the RFID reader and its associated antenna(s).

Figure 1:
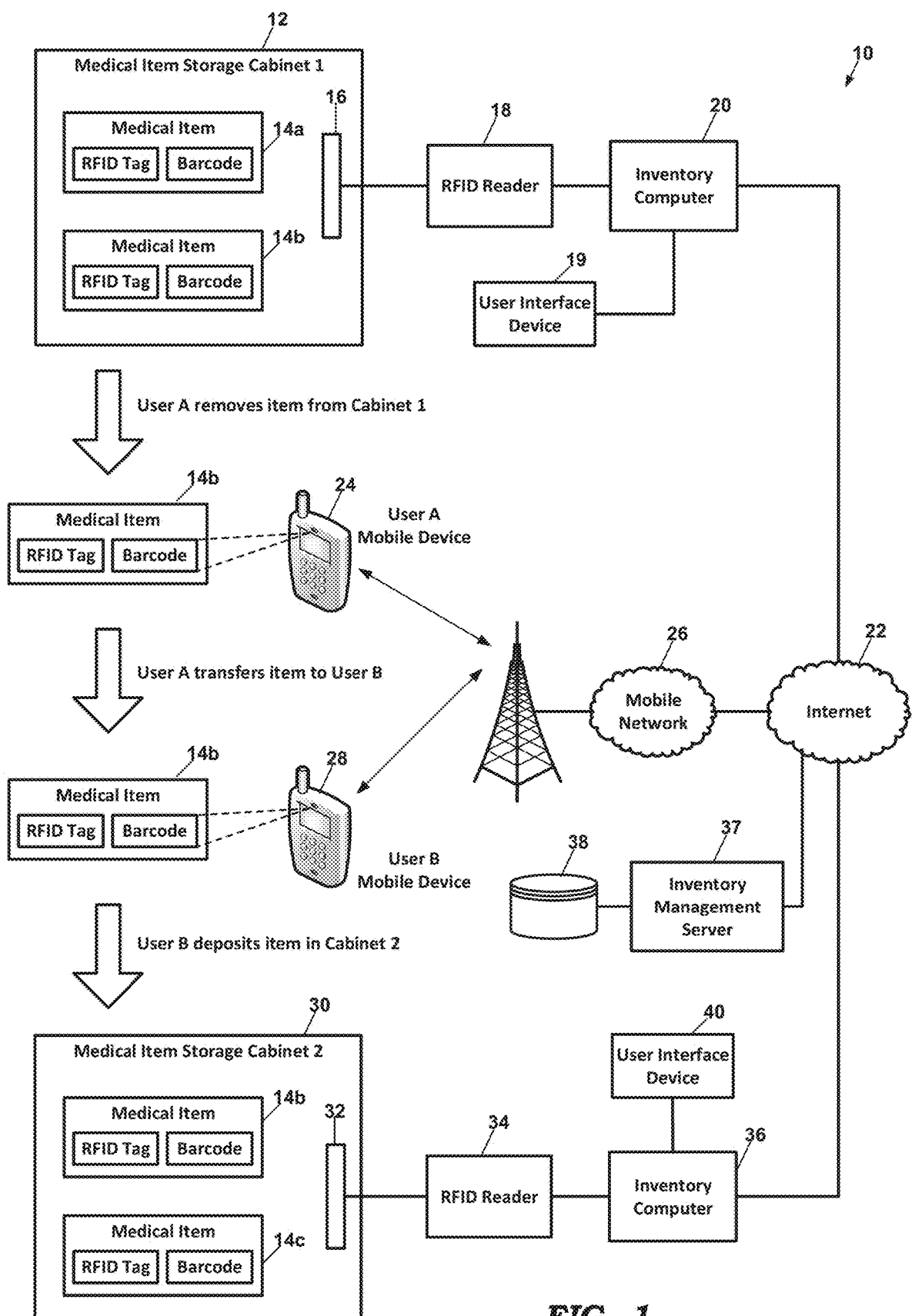
FIG. 1 depicts a system for managing medical item inventory and maintaining a digital chain of custody for medical items according to an embodiment of the invention.

FIG. 1 depicts an embodiment of a system 10 for automated management of medical item inventory and maintenance of a digital chain of custody for medical items. The system 10 includes a first access-controlled shielded enclosure 12 (also referred to herein as a first cabinet) having an interior space for receiving medical items, such as medical items 14a and 14b. Disposed within the cabinet 12 is an RFID antenna 16, such as a Laird Far Field antenna having left-hand circular polarization and operating in the 902-928 MHz frequency range. The RFID antenna 16 is electrically connected, such as via a coaxial cable, to a UHF RFID tag reader 18, such as an Impinj® Speedway® model R420.

As the term is used herein, "shielded" means that the cabinet 12 is designed to prevent the antenna 16 from receiving RFID signals from RFID tags located outside the cabinet 12 at a signal-to-noise ratio high enough to trigger detection of those outside RFID tags. For purposes of this disclosure, "shielded" does not mean that absolutely all RF energy is blocked from entering the cabinet, as this would require unnecessary levels of shielding.

The RFID tag reader 18 is electrically connected via a local area network (LAN) to a medical item inventory computer 20, which may be a server computer, desktop computer, laptop computer, tablet computer or other mobile computing device. Alternatively, the electrical connection between the RFID tag reader 18 and the computer 20 is via a Universal Serial Bus (USB) interface or other serial interface. The computer 20 includes memory for storing and a processor for executing instructions for updating and maintaining inventory records as described in more detail herein. In a preferred embodiment, the computer 20 is built into a door of the cabinet 12 through which medical items are added or removed. A user interface device 19 is connected to the computer 20, which may be used to receive user identification credentials. The user interface device 19 may include one or more of a touch screen display, a keypad, a biometric sensor such as a fingerprint reader or retinal scanner, and a code reader, such as an RFID reader, barcode reader or magnetic stripe reader. Such interface components may be used to read or otherwise receive identification information of personnel seeking access to the cabinet 12.

The computer 20 may be programmed to keep the door of the cabinet 12 locked while an RFID scan is taking place so as not to detect RFID tags on items outside the cabinet 12. Alternatively, the computer 20 may be programmed to deactivate the RFID reader 18 when the cabinet door is open to avoid reading RFID tags on items outside the cabinet.

In a preferred embodiment, the inventory computer 20 is in communication with a wide area communication network 22, such as the Internet, through which the computer 20 communicates with an inventory management server 37 and a medical item inventory database 38. In an alternative embodiment, the computer 20 communicates with the server 37 and database 38 via a local area network. The inventory database 38, which may be maintained by an inventory service provider entity, stores information regarding medical items, including item EPCs, the identity of a person having custody of an item, and information identifying a location, such as an inventory storage cabinet, in which a medical item is stored. In a preferred embodiment, the inventory management server 37 executes software instructions for communicating with inventory computers 20 and 36 and mobile devices 24 and 28, and for processing inventory records stored in the database 38.

As shown in FIG. 1, the system 10 may also include a second access-controlled shielded enclosure 30 (also referred to herein as a second cabinet) having an interior space for receiving medical items, such as medical items 14b and 14c. The second cabinet 30 may be in the same or a different medical facility as the first cabinet 12, or it may be in an office or home of a medical device sales representative. Disposed within the cabinet 30 is an RFID antenna 32 that is electrically connected to a UHF RFID tag reader 34. The RFID tag reader 34 is electrically connected via a LAN to a second medical item inventory computer 36, which may be a server computer, desktop computer, laptop computer, tablet computer or other mobile computing device. Alternatively, the electrical connection between the RFID tag reader 34 and the computer 36 is via a USB interface or other serial interface. Like the computer 20, the computer 36 includes memory for storing and a processor for executing instructions for updating and maintaining inventory records. In a preferred embodiment, the computer 36 is built into a door of the cabinet 30 through which medical items are added or removed. A user interface device 40 is connected to the computer 36, which may be used to receive user identification credentials. The user interface device 40 may include a touch screen display, a keypad, a biometric sensor such as a fingerprint reader or retinal scanner, and a code reader, such as an RFID reader, barcode reader or magnetic stripe reader. Such interface components may be used to read or otherwise receive identification information of personnel seeking access to the cabinet 30.

The system 10 also includes a first user's mobile computing device 24 and a second user's mobile computing device 28. The devices 24 and 28 may be smart phones, tablet computers, or other mobile computing devices having cameras for acquiring an image of a 2D barcode. The first and second users are also referred to herein as User A and User B, respectively. The mobile computing devices 24 and 28 are in communication with one or more mobile communication networks 26, such as a cellular data network, which is in communication with the network 22.

Figure 2:
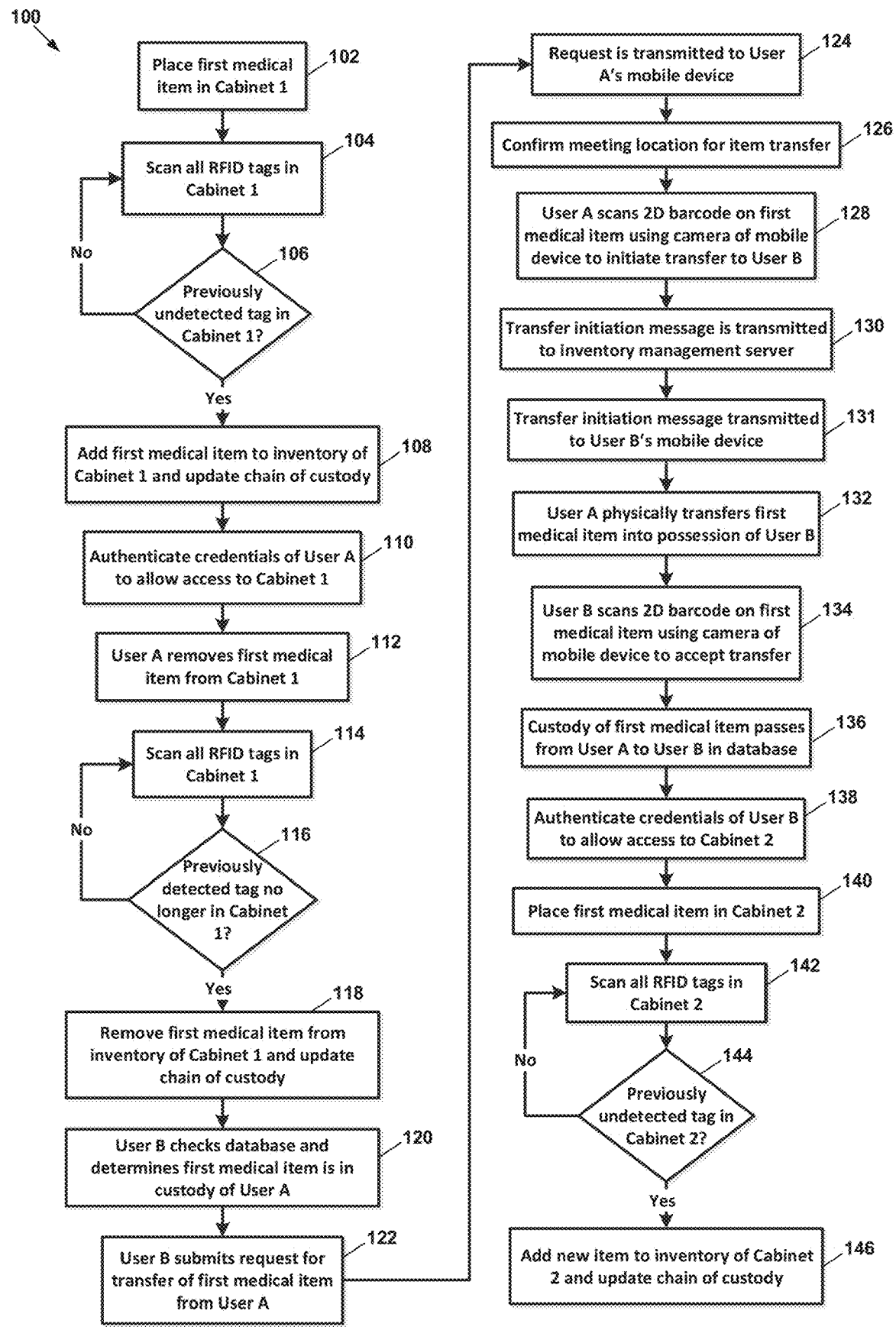
FIG. 2 depicts an embodiment of a method for managing medical item inventory and maintaining a digital chain of custody for medical items using the system of FIG. 1.

FIG. 2 depicts a method for managing medical device inventories and maintaining a digital chain of custody for medical devices using the system of FIG. 1. At some time after a medical item has been placed in the first cabinet 12 (step 102), the RFID reader 18 scans RFID tags on all of the medical items stored in the first cabinet 12 (step 104). If an RFID tag is detected that was not detected in a previous scan (step 106), the system determines that a newly-added medical item is in the cabinet 12, and the unique identifier, preferably the EPC, of the new item is added to the inventory records stored in the database 38 (step 108). The chain of custody of the newly-detected item is also updated in the database 38 to indicate that the item is no longer in the custody of a person.

At some point, a particular medical item stored in the cabinet 12 may be needed for a medical procedure or some other purpose. Medical personnel, referred to hereinafter as User A, uses the user interface device 19 to authenticate User A's credentials, thereby gaining access to the first cabinet 12 (step 110). User A removes the first medical item 14a from the cabinet 12 and closes the cabinet door (step 112), after which the RFID reader 18 scans RFID tags on all medical items remaining in the first cabinet 12 (step 114). If an RFID tag is not detected that was detected during a previous scan (step 116), the system determines that a medical item has been removed from the cabinet 12. The inventory records associated with the unique identifier of the removed item 14a are then updated in the database 38 to indicate that the item 14a is no longer in the first cabinet 12 (step 118). The chain of custody of the item 14a is also updated in the database 38 to indicate that the removed item is now in the custody of User A.

After removal of the item 14a from the cabinet 12, another medical personnel, referred to hereinafter as User B, determines that the medical item 14a is needed for another medical procedure or some other purpose. User B accesses the database 38, such as using a software application running on User B's mobile device 28, and determines that the medical item 14a is in the custody of User A (step 120). Using the software application running on User B's mobile device 28, User B submits a request for a transfer of the medical item 14a from User A to User B (step 122). This transfer request is preferably in the form of a first transfer request message transmitted from User B's mobile device 28. The inventory management server 37 receives and processes User B's request, and if the database records confirm that the medical item 14a is in the custody of User A, the server 37 transmits a second transfer request message to User A's mobile device 24 (step 124) to be displayed thereon. In a preferred embodiment, the second transfer request message identifies the medical device 14a, such as by EPC number, identifies User B as the requesting party, and provides contact information for User B, such as an email address or phone number.

User A and User B then communicate and determine a location at which to meet to physically transfer the medical item 14a from User A to User B (step 126). Either prior to or during the meeting, User A scans the 2D barcode attached to the medical item 14a using User A's mobile device 24. A software application running on User A's mobile device 24 decodes the unique identifier encoded in the 2D barcode to initiate a transfer of the medical item 14a to User B (step 128). In a preferred embodiment, the software application on User A's mobile device 24 transmits a first transfer initiation message with the item's unique identifier to the inventory management server 37, which correlates this first transfer initiation message with the earlier transfer request for the same item sent by User B's mobile device 28 (step 130). The inventory management server 37 then transmits a second transfer initiation message to User B's mobile device 28 on which the message is displayed to prompt User B to scan the 2D barcode attached to the medical item 14a (step 131).

After User A hands over the medical item 14a to User B (step 132), User B scans the 2D barcode attached to the medical item 14a using User B's mobile device 28. A software application running on User B's mobile device 28 decodes the unique identifier encoded in the 2D barcode to accept the transfer of the medical item 14a to User B (step 134). In a preferred embodiment, the software application on User B's mobile device 24 transmits a transfer confirmation message with the item's unique identifier to the inventory management server 37, which updates the records stored in the database 38 to reflect that custody of the item 14a has passed from User A to User B (step 136).

At some later time, User B may want to store the medical item 14a in a secure location, such as the storage cabinet 30, thereby relinquishing custody of the item. To do so, User B uses the user interface device 40 to authenticate User B's credentials, thereby gaining access to the second cabinet 30 (step 138). User B places the first medical item 14a into the cabinet 30 and closes the cabinet door (step 140), after which the RFID reader 34 scans RFID tags on all medical items stored in the second cabinet 30 (step 142). If an RFID tag is detected that was not detected during a previous scan (step 144), the system determines that a new medical item has been placed in the cabinet 30. The inventory management server 37 then updates the records associated with the EPC of the newly-added item in the database 38 to indicate that the item 14a is now in the second cabinet 30 (step 146). The chain of custody of the item 14a is also updated in the database 38 to reflect that the item is no longer in the custody of User B.

Preferred embodiments described herein use a 2D barcode in combination with an RFID tag on an item label to encode information regarding the item. It will be appreciated that other types of optical encoding devices could be used, such as standard one-dimensional barcodes, for the same purpose. Thus, embodiments of the invention are not limited to the use of 2D barcodes.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for maintaining a digital chain of custody of a medical item to which an RFID tag and an optical code are attached, both of which encode a unique identifier that uniquely identifies the medical item, wherein the digital chain of custody comprises a digital record of transfers of custody of medical items from user to user that is stored in a medical item inventory database, the method comprising:
   (a1) providing a shielded enclosure having an interior space and a lockable door, wherein the shielded enclosure is configured to attenuate radio frequency signals emanated from RFID tags disposed outside the shielded enclosure to levels that are substantially undetectable within the interior space, wherein access to the interior space is made via the lockable door that is controlled by an inventory computer;
   (a2) disposing an RFID antenna within the interior space of the shielded enclosure;
   (a3) disposing the medical item within the interior space of the shielded enclosure;
   (b) performing a first scan of the interior space of the shielded enclosure using an RFID reader connected to the RFID antenna and detecting the RFID tag attached to the medical item;
   (c) decoding the unique identifier encoded in the RFID tag attached to the medical item using the RFID reader;
   (d) storing the unique identifier in the medical item inventory database in association with information identifying the shielded enclosure;
   (e) receiving first user identification information at the inventory computer and verifying that the first user identification information is associated with a first user who is authorized to access the interior space of the shielded enclosure;
   (f) upon verification of the first user identification information, the inventory computer unlocking the door of the shielded enclosure to provide access thereto;
   (g) the first user removing the medical item from the shielded enclosure;
   (h) after step (g), performing a scan of the interior space of the shielded enclosure using the RFID reader and determining that the medical item is no longer within the shielded enclosure based on the RFID tag attached to the medical item that was detected during the first scan being not detected during the subsequent scan;
   (i) based on a determination that the medical item is no longer within the shielded enclosure, updating the digital chain of custody of the medical item by associating the unique identifier of the medical item with the first user identification information in the medical item inventory database;
   (j) after step (i), scanning the optical code attached to the medical item using a mobile computing device associated with a second user;
   (k) decoding the unique identifier encoded in the optical code attached to the medical item; and
   (l) an inventory management server computer updating the digital chain of custody of the medical item by associating the unique identifier of the medical item in the medical item inventory database with second user identification information that identifies the second user, thereby indicating that custody of the first medical item has passed from the first user to the second user.

2. The method of claim 1 wherein step (1) further comprises the inventory management server computer updating the digital chain of custody of the medical item by disassociating in the medical item inventory database the unique identifier decoded in step (k) with the first user identification information.

3. The method of claim 1 further comprising, prior to step (j), the mobile computing device associated with the second user submitting a query to the medical item inventory database to determine one or more of a location at which the medical item is stored and an identity of a person having custody of the medical item.

4. The method of claim 1 further comprising, prior to step (j):
   the mobile computing device associated with the second user transmitting a first transfer request message to request a transfer of custody of the medical item to the second user from the first user identified by the first user identification information;
   an inventory management server computer receiving the first transfer request message and transmitting a second transfer request message to a mobile computing device associated with the first user; and
   the mobile computing device associated with the first user receiving the second transfer request message and displaying the second transfer request message to the first user.

5. The method of claim 4 further comprising, prior to step (j):
   scanning the optical code attached to the medical item using the mobile computing device associated with the first user;
   decoding the unique identifier encoded in the optical code attached to the medical item using the mobile computing device associated with the first user;
   the mobile computing device associated with the first user transmitting a first transfer initiation message to initiate a transfer of custody of the medical item to the second user from the first user;
   the inventory management server computer receiving the first transfer initiation message and, based thereon, transmitting a second transfer initiation message to the mobile computing device associated with the second user; and
   the mobile computing device associated with the second user receiving the second transfer initiation message and displaying the second transfer initiation message to prompt the second user to proceed with step (j).

6. The method of claim 1 further comprising, after step (k) and before step (1):
   the mobile computing device associated with the second user transmitting a transfer confirmation message containing the unique identifier of the medical item; and
   the inventory management server computer performing step (1) upon receipt of the transfer confirmation message.

7. The method of claim 1 wherein the optical code comprises a two-dimensional barcode.

8. A method for maintaining a digital chain of custody of medical items that each have an RFID tag and an optical code attached thereto, both of which encode a unique identifier that uniquely identifies a medical item, wherein the digital chain of custody comprises a digital record of transfers of custody of medical items from user to user that is stored in a medical item inventory database, the method comprising:

(a1) providing a shielded enclosure having an interior space, wherein the shielded enclosure is configured to attenuate radio frequency signals emanated from RFID tags disposed outside the shielded enclosure to levels that are substantially undetectable within the interior space;

(a2) disposing an RFID antenna within the interior space of the shielded enclosure;

(a3) storing medical items within the interior space of the shielded enclosure;

(a4) performing a scan of the interior space of the shielded enclosure in which the medical items are stored, the scan performed using an RFID reader connected to the RFID antenna;

(b) based on the scan of step (a4) not detecting an RFID tag attached to a first medical item that was detected during a previous scan, determining that the first medical item has been removed from the shielded enclosure;

(c) based on a determination that the first medical item has been removed from the shielded enclosure, updating the digital chain of custody of the first medical item by associating the unique identifier of the first medical item with first user identification information in a medical item inventory database, where the first user identification information identifies a first user who removed the first medical item from the shielded enclosure;

(d) scanning the optical code attached to the first medical item using a mobile computing device associated with a second user;

(e) decoding the unique identifier encoded in the optical code attached to the first medical item; and (f) updating the digital chain of custody of the first medical item by associating in the medical item inventory database the unique identifier decoded in step (e) with second user identification information that identifies the second user, thereby indicating that custody of the first medical item has passed from the first user to the second user.

9. The method of claim 8 wherein step (f) further comprises updating the digital chain of custody of the first medical item by disassociating in the medical item inventory database the unique identifier decoded in step (e) with the first user identification information.

10. A method for maintaining a digital chain of custody of a medical item to which an RFID tag and an optical code are attached, both of which encode a unique identifier that uniquely identifies the medical item, wherein the digital chain of custody comprises a digital record of transfers of custody of medical items from user to user that is stored in a medical item inventory database, the method comprising:

(a) providing a shielded enclosure having an interior space and a lockable door, wherein the shielded enclosure is configured to attenuate radio frequency signals emanated from RFID tags disposed outside the shielded enclosure to levels that are substantially undetectable within the interior space, wherein an RFID antenna is disposed within the interior space, wherein access to the interior space is made via the lockable door that is controlled by an inventory computer;

(b) disposing the medical item within the interior space of the shielded enclosure;

(c) performing a scan of the interior space of the shielded enclosure using an RFID reader connected to the RFID antenna and detecting the RFID tag attached to the medical item;

(d) decoding the unique identifier encoded in the RFID tag attached to the medical item using the RFID reader;

(e) storing the unique identifier in the medical item inventory database in association with information identifying the shielded enclosure;

(f) receiving first user identification information at the inventory computer and verifying that the first user identification information is associated with a first user who is authorized to access the interior space of the shielded enclosure;

(g) upon verification of the first user identification information, the inventory computer unlocking the door of the shielded enclosure to provide access thereto;

(h) the first user removing the medical item from the shielded enclosure;

(i) after step (h), performing a subsequent scan of the interior space of the shielded enclosure using the RFID reader and determining that the medical item is no longer within the shielded enclosure based on the RFID tag attached to the medical item that was detected during the scan of step (c) being not detected during the subsequent scan;

(j) based on a determination that the medical item is no longer within the shielded enclosure, updating the digital chain of custody of the medical item by associating the unique identifier of the medical item with the first user identification information in the medical item inventory database;

(k) after step (j), scanning the optical code attached to the medical item using a mobile computing device associated with a second user;

(l) decoding the unique identifier encoded in the optical code attached to the medical item;

(m) the mobile computing device associated with the second user transmitting a transfer confirmation message containing the unique identifier of the medical item; and (n) upon receipt of the transfer confirmation message, updating the digital chain of custody of the medical item by
associating the unique identifier of the medical item in the medical item inventory database with second user identification information that identifies the second user; and
disassociating in the medical item inventory database the unique identifier decoded in step (1) with the first user identification information.

11. The method of claim 10 further comprising, prior to step (k), the mobile computing device associated with the second user submitting a query to the medical item inventory database to determine one or more of a location at which the medical item is stored and an identity of a person having custody of the medical item.

12. The method of claim 10 further comprising, prior to step (k):
the mobile computing device associated with the second user transmitting a first transfer request message to request a transfer of custody of the medical item to the second user from the first user identified by the first user identification information;

an inventory management server computer receiving the first transfer request message and transmitting a second transfer request message to a mobile computing device associated with the first user; and the mobile computing device associated with the first user receiving the second transfer request message and displaying the second transfer request message to the first user.

13. The method of claim 12 further comprising, prior to step (k):

scanning the optical code attached to the medical item using the mobile computing device associated with the first user;

decoding the unique identifier encoded in the optical code attached to the medical item using the mobile computing device associated with the first user;

the mobile computing device associated with the first user transmitting a first transfer initiation message to initiate a transfer of custody of the medical item to the second user from the first user;

the inventory management server computer receiving the first transfer initiation message and, based thereon, transmitting a second transfer initiation message to the mobile computing device associated with the second user; and the mobile computing device associated with the second user receiving the second transfer initiation message and displaying the second transfer initiation message to prompt the second user to proceed with step (k).

* * * * *